United States Patent
Piracha et al.

(10) Patent No.: US 10,639,442 B2
(45) Date of Patent: May 5, 2020

(54) VENTILATION APPARATUS

(71) Applicant: Umbulizer LLC, Cambridge, MA (US)

(72) Inventors: Shaheer Ahmed Piracha, Cambridge, MA (US); Sanchay Gupta, Boston, MA (US); Rohan Jadeja, Westborough, MA (US); Wasay Anwer, Cambridge, MA (US)

(73) Assignee: Umbulizer LLC, Cambridge, MA (US)

( * ) Notice: Subject to any disclaimer, the term of this patent is extended or adjusted under 35 U.S.C. 154(b) by 0 days.

(21) Appl. No.: 16/403,254

(22) Filed: May 3, 2019

(65) Prior Publication Data

US 2019/0336713 A1    Nov. 7, 2019

Related U.S. Application Data

(60) Provisional application No. 62/666,403, filed on May 3, 2018.

(51) Int. Cl.
  *A61M 16/00* (2006.01)
  *A61M 16/20* (2006.01)
  *A61M 16/10* (2006.01)

(52) U.S. Cl.
  CPC ...... *A61M 16/0078* (2013.01); *A61M 16/024* (2017.08); *A61M 16/208* (2013.01);
  (Continued)

(58) Field of Classification Search
  CPC ............ A61M 16/0078; A61M 16/208; A61M 16/024; A61M 16/022; A61M 16/0084;
  (Continued)

(56) References Cited

U.S. PATENT DOCUMENTS

| 2,595,493 A | * | 5/1952 | Slaby | ...................... B01L 3/021 |
| | | | | 73/864.11 |
| 7,578,293 B2 | | 8/2009 | Matthiessen et al. | |

(Continued)

FOREIGN PATENT DOCUMENTS

| WO | 2016-196837 A1 | 12/2016 |
| WO | 2018-065448 A1 | 4/2018 |

OTHER PUBLICATIONS

Hussain, Abdul Mohsen Al, et al.—"Design and Prototyping of a Low-cost Portable Mechanical Ventilator," Proceedings of the 2010 Design of Medical Devices Conference (DMD2010-3845), Apr. 13-15, 2010, Minneapolis, MN, USA, 9 pages.

(Continued)

*Primary Examiner* — Timothy A Stanis
*Assistant Examiner* — Margaret M Luarca
(74) *Attorney, Agent, or Firm* — Nutter McClennan & Fish LLP

(57) ABSTRACT

A method of ventilating a patient controls an actuator, in accordance with a prescribed value for a respiratory parameter, to compress an inflatable bag to cause air to flow out of an output valve of the bag. The respiratory parameter may include tidal volume, pressure, volume limit, peak pressure, I:E ratio, inspiratory time, and/or breathing rate of the air flowing through the output valve. The method also senses the pressure flowing through the output valve, and sends a pressure signal to the controller. Additionally, the method senses the flow rate through the output valve, and sends a flow rate signal to the controller. The method also adjusts the compression of the actuator as a function of the flow rate signal and/or the pressure signal to adjust the output tidal volume, pressure, volume limit, peak pressure, I:E ratio, inspiratory time, and/or breathing rate to be in accordance with the prescribed value.

19 Claims, 6 Drawing Sheets

(52) U.S. Cl.
CPC ............... *A61M 2016/0027* (2013.01); *A61M 2016/0033* (2013.01); *A61M 2016/1025* (2013.01); *A61M 2230/42* (2013.01)

(58) Field of Classification Search
CPC .......... A61M 16/0081; A61M 16/0075; A61M 16/209; A61M 16/0069
See application file for complete search history.

(56) References Cited

U.S. PATENT DOCUMENTS

| | | |
|---|---|---|
| 8,534,282 B2 | 9/2013 | Bergman |
| 10,137,265 B2 | 11/2018 | Freeman et al. |
| 2005/0199237 A1 | 9/2005 | Lurie |
| 2005/0284472 A1 | 12/2005 | Lin |
| 2013/0118498 A1 | 5/2013 | Robitaille et al. |
| 2014/0000613 A1 | 1/2014 | Hines |
| 2014/0005544 A1 | 1/2014 | Zalev et al. |
| 2014/0005566 A1 | 1/2014 | Homuth et al. |
| 2015/0283342 A1* | 10/2015 | Mielcarz .............. G09B 23/288 128/202.22 |
| 2017/0157348 A1 | 6/2017 | Gillespie et al. |
| 2017/0197047 A1 | 7/2017 | Minato et al. |
| 2018/0160970 A1 | 6/2018 | Khoury et al. |
| 2018/0311452 A1 | 11/2018 | Walker |

OTHER PUBLICATIONS

International Searching Authority—International Search Report for International Application No. PCT/US19/30692, dated Jul. 12, 2019, together with the Written Opinion of the International Searching Authority, 14 pages.

Government of Pakistan, Intellectual Property Organization—Pakistan Patent Application No. 483/2017, filed Sep. 18, 2017 along with Receipt No. 75561, 25 pages.

* cited by examiner

VENTILATION APPARATUS

PRIORITY

This patent application claims priority from provisional U.S. patent application No. 62/666,403, filed May 3, 2018, entitled, "VENTILATION APPARATUS," and naming Shaheer Ahmed Piracha as inventor, the disclosure of which is incorporated herein, in its entirety, by reference.

FIELD OF THE INVENTION

Illustrative embodiments of the invention generally relate to ventilation devices and, more particularly, the various embodiments relate to systems and methods for precisely ventilating a patient in accordance with prescribed parameters.

BACKGROUND OF THE INVENTION

Respiratory disease is one of the leading causes of death in many developing countries. Frequently, there is a shortage of life saving equipment, like ventilators, at hospitals in these countries. As a result, caregivers are often provided with a bag valve mask or Ambu bag and asked to manually ventilate a patient by hand for hours and sometimes days. This arrangement is unreliable can may be life threatening to the patient.

SUMMARY OF VARIOUS EMBODIMENTS

In accordance with one embodiment of the invention, a system ventilates a patient. The system includes a bag that is configured to be inflated through an input valve that allows oxygen and/or air to flow into the bag. The bag is further configured to be deflated through an output valve that allows the oxygen and/or the air to flow out of the bag. The system also includes an actuator configured to compress the bag to cause the oxygen and/or the air to flow out of the output valve in accordance with prescribed values for one or more respiratory parameter. The one or more respiratory parameter includes tidal volume, pressure, volume limit, peak pressure, I:E ratio, inspiratory time, and/or breathing rate of the oxygen and/or the air flowing through the output valve to a patient. The system also has a controller configured to control the position of the actuator and/or the speed at which the actuator moves in accordance with the prescribed values for the respiratory parameter. Furthermore, the system includes a pressure sensor coupled to the output valve and configured to determine the pressure of the oxygen and/or the air flowing through the output valve. The pressure sensor is further configured to send a pressure signal to the controller. The system also includes a flow rate sensor coupled to the output valve and configured to determine the flow rate of the oxygen and/or the air flowing through the output valve. The flow rate sensor is further configured to send a flow rate signal to the controller. The controller is configured to receive the pressure signal and/or the flow rate signal, and to determine whether the output tidal volume, pressure, volume limit, peak pressure, I:E ratio, inspiratory time, and/or breathing rate are in accordance with the prescribed values. Additionally, the controller is further configured to adjust the position of the actuator and/or the speed at which the actuator moves so as to adjust the output tidal volume, peak pressure, and/or breathing rate to be in accordance with the prescribed values.

In some settings, the bag may be an Ambu bag. The bag may be compressed in accordance with respiratory parameters that include an inhale to exhale ratio. To that end, the bag may be compressed between the paddle and a flat surface. Furthermore, the flat surface may be a fixed surface. In some embodiments the actuator has a convex contact surface that compresses the bag. Furthermore, the bag may have a longitudinal axis, and the convex contact surface may be configured to extend along the longitudinal axis. The system may perform a calibration process to confirm that the bag is outputting air in accordance with one or more prescribed respiratory parameter.

Among other things, the actuator may include a spindle that is configured to tighten a strap. The strap may be coupled to a paddle having the convex contact surface. The strap may have a first end that is fixed, and a second end that is movable.

In some embodiments, the system is configured to operate in a volume control mode. The volume control mode includes a prescribed value for the tidal volume, and a prescribed limit for the peak pressure. Alternatively, the system may be configured to operate in a pressure control mode. The pressure control mode includes a prescribed value for the pressure, and a prescribed volume limit. Among other things, an alert may be trigged and/or the actuator may cease ventilating the patient when the prescribed limit is exceeded.

Additionally, or alternatively, to the flow rate sensor and/or the pressure sensor, the system may also have an oxygen sensor. Each of the sensors may be coupled to a display that shows information relating to the sensor. In some embodiments, the display may be coupled to a user input that allows the user to adjust the oxygen input.

In accordance with yet another embodiment, a method ventilates a patient. The method includes controlling an actuator, in accordance with a prescribed value for a respiratory parameter, to compress an inflatable bag to cause oxygen and/or air to flow out of an output valve of the bag. The respiratory parameter may include tidal volume, pressure, volume limit, peak pressure, I:E ratio, inspiratory time, and/or breathing rate of the oxygen and/or the air flowing through the output valve. The method also senses the pressure flowing through the output valve, and sends a pressure signal to the controller. Additionally, the method senses the flow rate through the output valve, and sends a flow rate signal to the controller. The method also adjusts the compression of the actuator as a function of the flow rate signal and/or the pressure signal to adjust the output tidal volume, pressure, volume limit, peak pressure, I:E ratio, inspiratory time, and/or breathing rate to be in accordance with the prescribed value.

In some embodiments, the method couples the actuator to a paddle having a longitudinal axis. Additionally, the method may substantially align the longitudinal axis of the paddle with a longitudinal axis of the bag. Furthermore, the method may adjust the compression of the actuator by adjusting the position of the actuator and/or the speed at which the actuator moves.

Illustrative embodiments of the invention are implemented as a computer program product having a computer usable medium with computer readable program code thereon. The computer readable code may be read and utilized by a computer system in accordance with conventional processes.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

DESCRIPTION OF ILLUSTRATIVE EMBODIMENTS

In illustrative embodiments, a ventilation apparatus provides reliable and precise ventilation to a patient in accordance with a set of prescribed respiratory parameters. The apparatus operates on an inflatable bag used to provide positive pressure ventilation to patients who are not breathing adequately. For example, the apparatus may operate with a bag valve mask (also referred to under the proprietary name "Ambu bag"). The operator is allowed to select values for one or more respiratory inputs. Sensors measure the output from the bag, and provide a feedback loop to a controller, which makes corresponding adjustments to an actuator. The actuator has a convex shaped contact surface and is oriented parallel to the longitudinal axis of the bag. Details of illustrative embodiments are discussed below.

Figure 1:
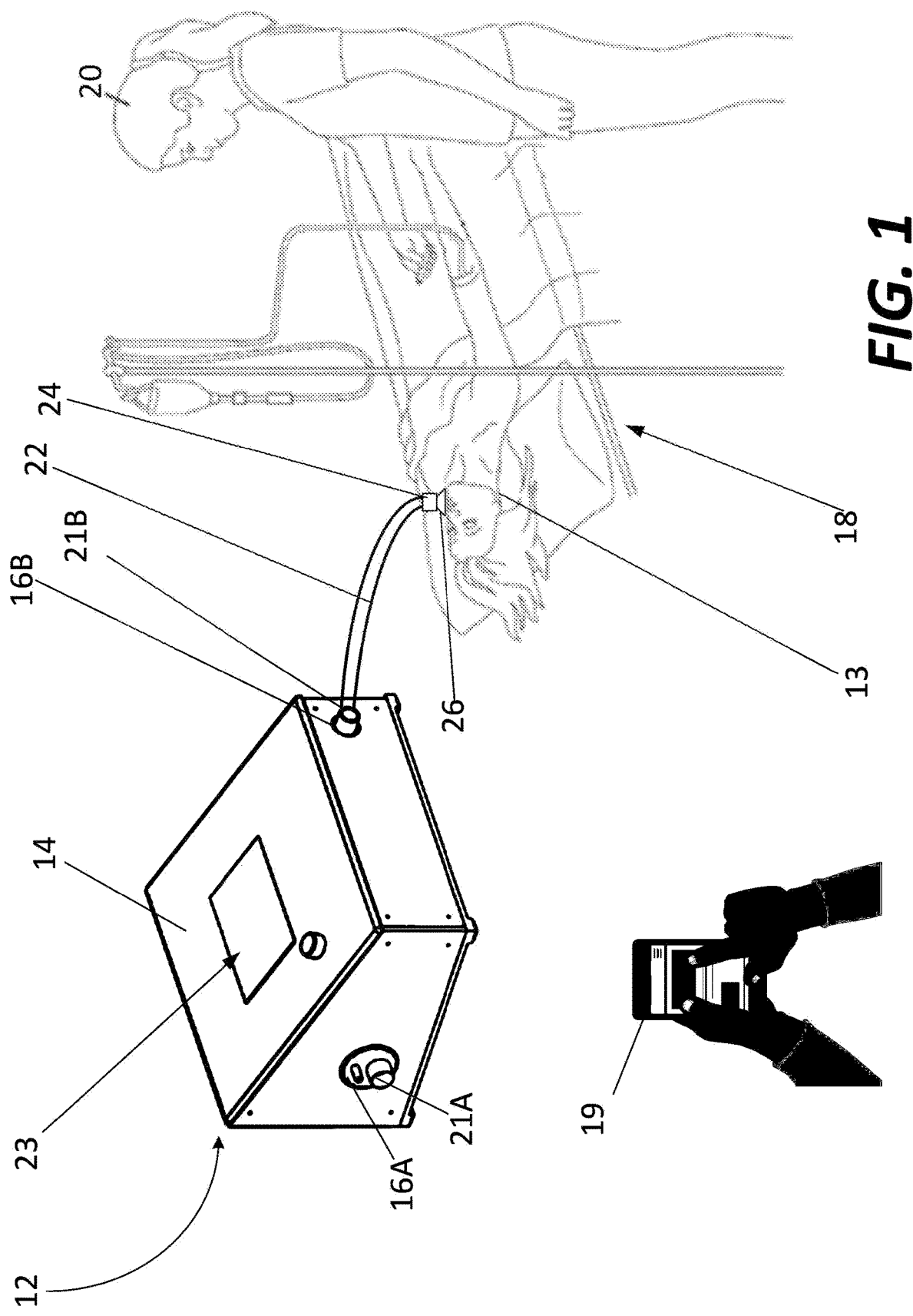
FIG. 1 schematically shows a ventilation device connected to a patient and a mobile application in accordance with illustrative embodiments of the invention.

FIG. 1 schematically shows the ventilation device 12 and a patient 13 in accordance with illustrative embodiments of the invention. The ventilation device 12 may have a housing 14 that contains the internal components. The housing 14 may have two openings 16A and/or 16B that accommodate two valves 21A and 21B, one for air input, and the other for air output, respectively. Preferably, each of these valves 21A and 21B is a one-way valve (e.g., input valve 21A only allows airflow into the device 12, output valve 21B only allows airflow out of the device 12). However, in some embodiments, the one-way valve 21B may additionally, or alternatively, be on the bag (see, for example, FIG. 2). Thus, the openings 16A and/or 16B may accommodate tubing that is part of a breathing circuit including the one-way valves 21A and 21B.

In FIG. 1, with the air input opening 16A is on the front side of the housing 14, and the air output opening 16B is on the side of the housing 14. It should be understood however that illustrative embodiments may have the openings 16A and 16B in various arrangements and orientations not shown herein, and are not intended to be limited to the arrangement shown herein. Although the term "air" is used with reference to the device 12, it should be understood that illustrative embodiments may use pure oxygen, or various gas combinations not found in the ambient air. Accordingly, the term "air" is not intended to limit illustrative embodiments to use only with ambient air in the environment. Indeed, the term "air" may include, among other things, pure oxygen provided by a commercial gas supplier.

The device 12 may be used in hospital or non-hospital settings, such as where the patient is laying on a hospital bed 18, emergency transport, in-field, etc. A breathing tube 22 may couple the output valve 21B to the patient 13. At the end of the breathing tube 22 may be another one way valve 24. The one way valve 24 may be similar to the valves 16A-16B that are found at the ends of a bag (e.g., the Ambu bag). The valve 24 provides one way ventilation that allows air to flow to the patient 13 while also preventing back flow of air in to the device 12. Accordingly, the valve(s) 24 and 21B may prevent contamination from entering back into the device 12. Additionally, illustrative embodiments may use a mask 26 and/or endotracheal tube 26 to couple the output valve 21B to the patient 13. The mask 26 and/or endotracheal tube 26 attaches to the end of one of the breathing tubes and inhibits air from escaping during the ventilation inhalation and exhalation cycle. The one way valve 26 may also provide for easy addition of a peep valve that is commonly used in resource-limited hospitals.

Many developing countries do not have an adequate number of ventilators for their patients 13. Instead, hospitals and emergency settings may require the use of the bags. Frequently, medical staff 20 or family members may be tasked with ventilating the patient 13 using the bag. However, proper ventilation of the patient 13 requires precise delivery of a given volume of air, at a given pressure, and at a given tempo for a sustained period of time, which is difficult to achieve even for trained staff 20.

Furthermore, the staff 20 may not have feedback about the pressure or flow rate that is used to ventilate the patient 13. Delivering air and/or oxygen in accordance with prescribed values for respiratory parameters is a more effective and safe manner of ventilating patients 13. For example, if the patient 13 receives too much tidal volume, the lungs may rupture or collapse. Additionally, if the patient 13 receives too much air pressure, the lung could be punctured and the patient 13 could have internal bleeding. If the air pressure is too low, the air and/or oxygen may not reach the lungs of the patient 13.

Even if feedback about the output parameters is provided to the staff 20, it is nearly impossible to manually ventilate the patient 13 consistently for a sustained period of time in accordance with the respiratory parameters. To further complicate matters, the input parameters for each patient 13 differ based on physiological differences in the patient 13 (e.g., height, body weight, age, etc.). Thus, even experienced staff 20 with feedback may have difficulty ventilating the patient 13 in accordance with appropriate parameters for a sustained period of time.

Accordingly, illustrative embodiments of the device 12 provide sensors that measure the output of the bag, and that provide feedback to a controller, which automatically adjusts an actuator to ventilate the patient 13 in accordance with the prescribed parameters. To that end, the device 12 may have a user interface 23, which may include a touch screen and/or a knob. The operator may enter the desired values to control a variety of respiratory parameters. For example, illustrative embodiments allow a user 20 to input respiratory parameters, including: Output Volume between about 0 and about 700 ml, Pressure Limit—between about 0 and about 50 mm $H_2O$, Breathing rate between about 1 and about 30 bpm, Inhalation to exhalation ratio of between about 1:0 and about 1:3, inspiratory time of between about 0.5 and about 3 seconds. The user interface 23 may provide the user secondary controls, including: switching between Pressure Control and Volume Control, changing power source from battery to power supply, oxygen titration based on % O2 reading on the screen, turning on/off Bluetooth, turning on/off Wi-Fi, turning Assist Control on/off. Furthermore, the system 100 may include alarms (e.g., for low battery, high pressure, disconnection of breathing tube) on the device 12, a display, or a mobile electronic device 19. Alarm tells the actuator to stop and go back to the reset position.

In addition to the user interface 23, illustrative embodiments may use a mobile electronic device 19 (such as smartphone 19 having a mobile app) to input the respiratory parameters. The values for the respiratory parameters may also be displayed on the mobile electronic device 19.

Figure 2:
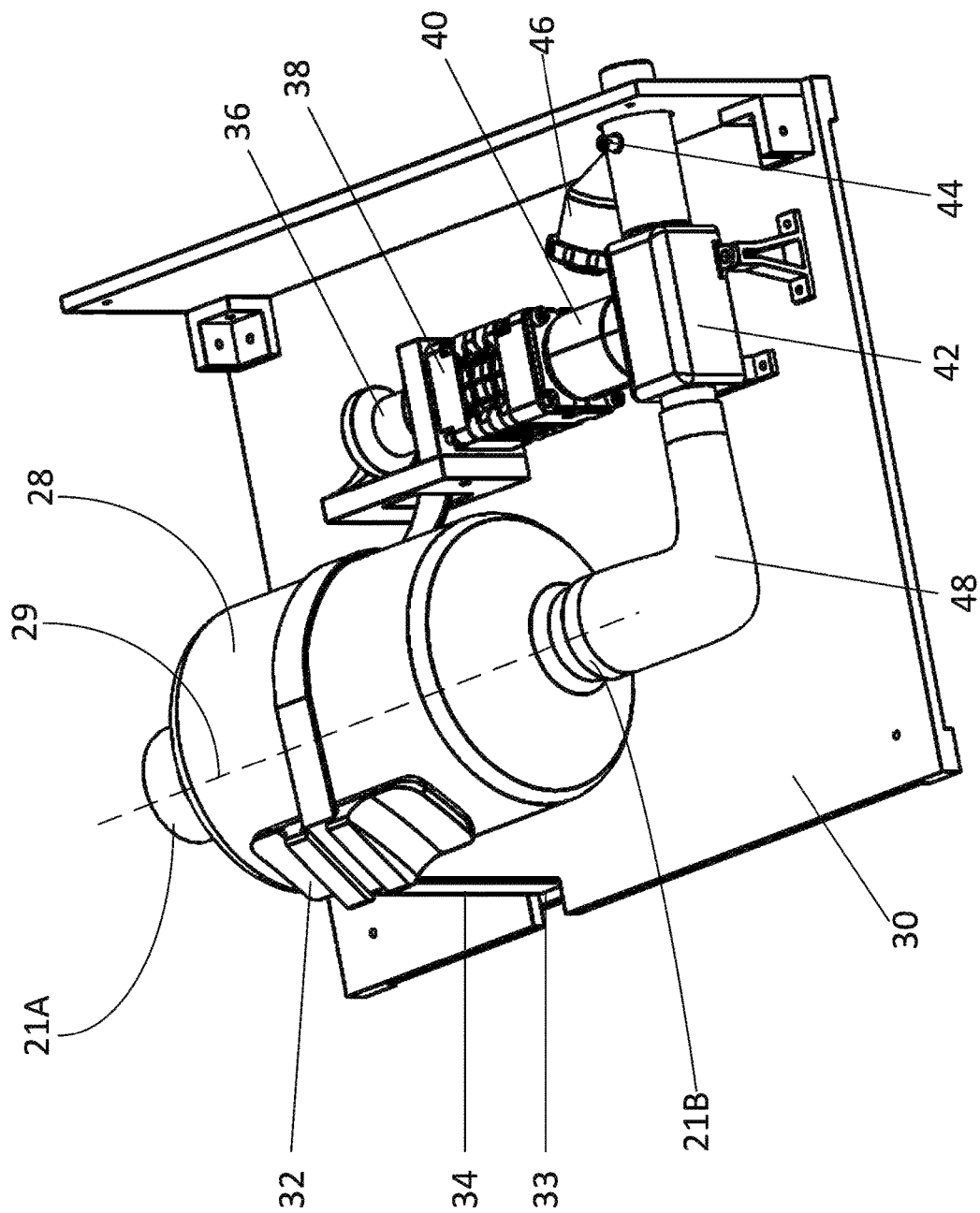
FIG. 2 schematically shows the internal components of the device in accordance with illustrative embodiments of the invention.

FIG. 2 schematically shows the internal components of the device 12 in accordance with illustrative embodiments of the invention. The device 12 may also include wires and electronics not shown herein for convenience. The device 12 may include a base 30 on which the internal components rest and/or are mounted. The device 12 includes an inflatable bag, such as the bag 28 (e.g., an Ambu bag). As described previously, the bag 28 may be inflated via air flow coming through input valve 21A. Additionally, the bag 28 may be deflated via air flow exiting through output valve 21B. Specifically, the bag 28 deflates as it is compressed by paddle 32. In some embodiments, the bag 28 is compressed between the paddle 32 and a flat surface such as the base 30.

As described further below, illustrative embodiments may include just a single convex contact surface 50 (e.g., a single paddle 32) to avoid creating dead space that may otherwise result from multi-directional inward compression (e.g., simultaneous compression from two convex paddles). For example, compressing the cylindrically shaped body of the bag 28 between two semi-spherical paddles 32 may create unintended dead space in the top and bottom quadrants of the bag 28. However, some other embodiments may include more than one paddle 32.

In illustrative embodiments the paddle 32 is coupled with a strap 34. At one end, the strap 34 may be fastened to the base 30 using a fastener 33. At the other end, the strap 34 may be coupled to an actuator that, when activated, tensions the strap 34. Thus, in illustrative embodiments, a first end of the strap 34 may be fixed, and a second end of the strap 34 may be movable. The inventors were surprised to discover that having one end of the strap 34 fixed, and the other end movable, provides the advantage of making the device 12 cleaner, smaller and efficient to drive and control precisely. Additionally, in comparison to multi-bar linkages, the strap 34 provides a simpler device 12 with lower rates of failure and easy maintenance. This is a significant advantage in certain markets where resources are limited. Tensioning the strap 34 causes the paddle 32 to inwardly radially compress the bag 28. As the bag 28 is compressed, air exits from the output valve 21B and the bag 28 deflates. It should be understood that the term deflate does not require that the bag 28 completely deflate. Indeed, the bag 28 may partially deflate in accordance with prescribed parameters.

In illustrative embodiments, the actuator includes a spindle 36 coupled to a motor 40 through a gear box and adapter 38. The inventors discovered that coupling the paddle 32 to the strap 34, and actuating compression of the bag 28 using a spindle 36 provides various advantages. For example, a paddle that is movable on a hinge undesirably puts a lot of load on the motor 40, which makes the device 12 more likely to fail. Given the emergency settings that the device 12 may be used in, it is desirable to have a robust device 12 that is easy to maintain, with fewer moving parts and lower rates of failure. In addition to requiring that the motor 40 work harder to achieve the same effects as illustrative embodiments using the strap 34, in the hinge arrangement the motor 40 moves very little to compress the bag a significant amount. Accordingly, illustrative embodiments using the strap 34 provide for convenient precision control of the volume of the bag.

Although not shown in FIG. 2, a controller may be coupled to the motor 40. The controller receives feedback from one or more sensors, and controls the output of the motor 40. For example, illustrative embodiments may include a flow sensor 42 coupled to the output valve 21B. Additionally, or alternatively, the device 12 may include a pressure sensor 44 coupled to the output valve 21B. Furthermore, an oxygen sensor 46 may additionally or alternatively be coupled to the output valve 21B. Although the various sensors 42, 44, and 46 are described as being coupled to the output valve 21B, it should be understood that they may not be directly coupled to the output valve 21B. For example, the sensors 42, 44, and 46 may be downstream of the valve 21B and connected via tubing 48. Accordingly, the sensors 42, 44, and 46 described herein advantageously provide information relating to the air output from the bag 28. These measurements can be directly correlated to specific respiratory parameters.

Figure 3B:
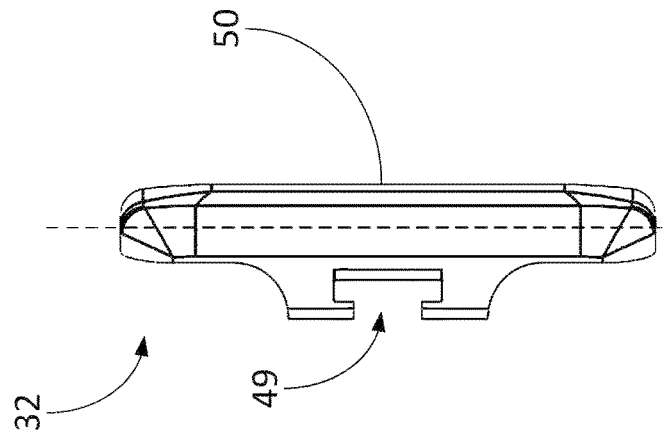
FIGS. 3A-3C schematically show views of a paddle for compressing a ventilation bag in accordance with illustrative embodiments of the invention.
Figure 3C:
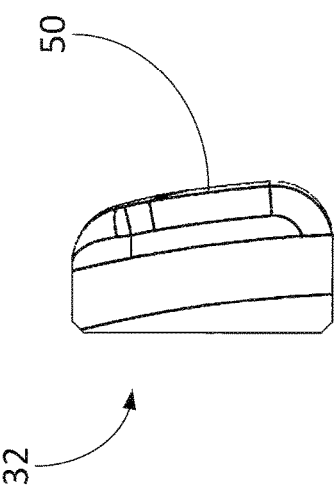
Figure 3A:
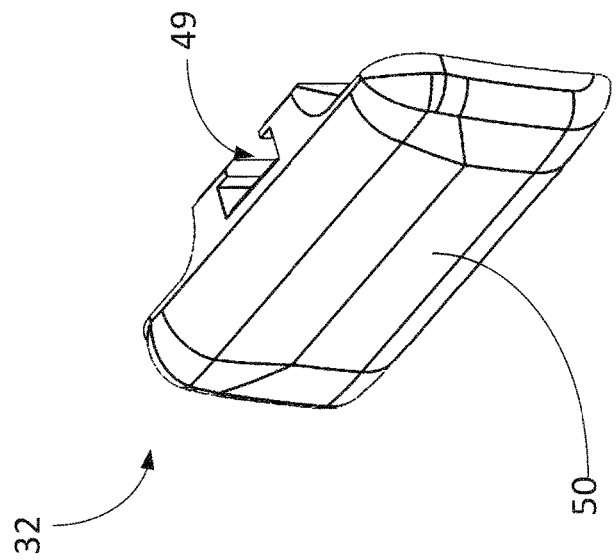

FIGS. 3A-3C schematically show the paddle 32 in accordance with illustrative embodiments of the invention. Specifically, FIG. 3A schematically shows a perspective view of the paddle 32. FIG. 3B schematically shows a left-side view of the paddle 32, and FIG. 3C schematically shows a top view of the paddle 32. The paddle 32 has a coupling portion 49, through which the paddle 32 is coupled to the strap 34. On the other end of the paddle 32 is a contact surface 50 that faces and compresses the bag 28.

The inventors were surprised to find that providing a convex contact surface 50 resulted in advantages over flat or concave contact surfaces 50. For example, a flat paddle 32 deforms the bag in a non-linear motion, meaning that the patient 13 experiences a sudden jump in flow rate and pressure. Additionally, flat paddles 32 create stress concentrations at the edges of the paddle and at the folding area of the bag 28. This could lead to faster degradation of the bag 28 and even critical leaks or tears over longer periods of time. A concave contact surface 50 leaves a large amount of dead space in the bag 28. Additionally, the concave contact surface 50 also causes a large spike in pressure and flow rate at the beginning of the compression cycle.

Accordingly, illustrative embodiments have a convex contact surface 50. Although the paddle 32 is described as having a convex contact surface 50, it should be understood that at least some portion of the surface area may be flat. Generally, however, the convex contact surface 50 allows for smaller buildup of pressure and flow, which is preferred in clinical settings. The convex contact surface 50 generally provides more precise deformation/compression of the bag 28, and leaves less dead space than other configurations.

In illustrative embodiments, the paddle 32 has a longitudinal axis 52 defined by its length. As shown in FIG. 2, the bag 28 also has a longitudinal axis 29 running through its length (e.g., an axis running through input valve 21A and output valve 21B). In illustrative embodiments, the longitudinal axis 52 of the paddle 32 is aligned with the longitudinal axis 29 of the bag 28 to inhibit the formation of dead space that may otherwise form during compression of the bag 28. By arranging the paddle 32 and the bag 28 so that their longitudinal axes 29 and 52 are substantially aligned, the bag 28 is more evenly compressed.

In some embodiments, the longitudinal axes 29 and 52 are less than 90 degrees offset from one another. Preferably, the longitudinal axes 29 and 52 are no more than 45 degrees offset from one another. In some embodiments, the longitudinal axes 29 and 52 are no more than 30 degrees offset from one another. In some embodiments, the longitudinal axes 29 and 52 are less than 10 degrees offset from one another. Additionally, to assist with reduction of dead space, in some embodiments, the length of the paddle 32 is at least 40% of the length of the body of the bag 28. More preferably, the length of the paddle 32 is greater than 50%, 60%, 70%, or 80% of the length of the body of the bag 28.

Figure 4:
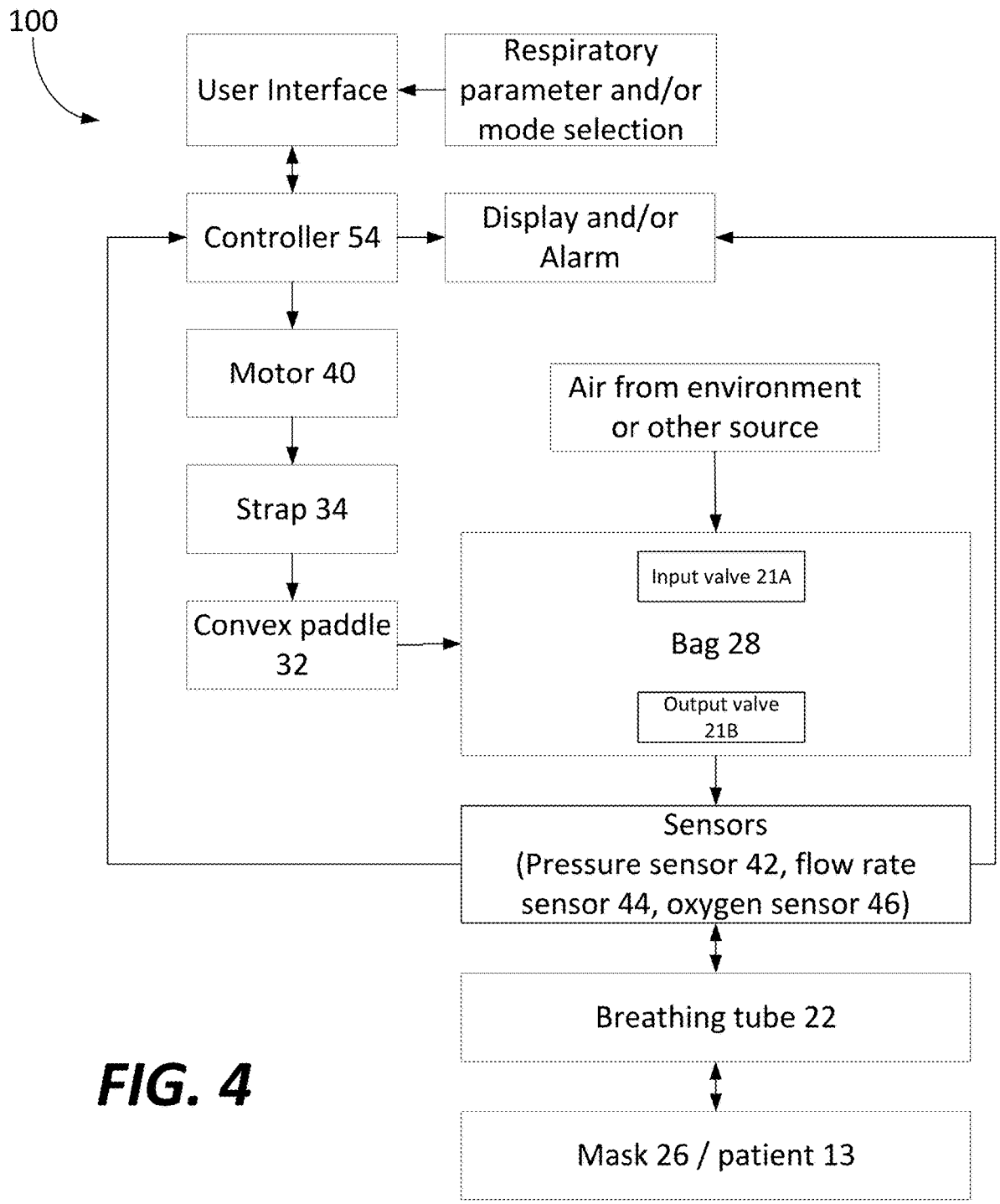
FIG. 4 schematically shows a block diagram of a system that uses the ventilation apparatus in accordance with illustrative embodiments of the invention.

FIG. 4 schematically shows a block diagram of a system 100 for ventilation in accordance with illustrative embodiments of the invention. Air enters the system 100 and optionally go through a filter, which filters contamination such as dust. The air may be received from the environment, and/or through connected gas cylinders that are commercially available (e.g., through commercial entities such as Airgas or equipment such as air compressors). In illustrative embodiments, the air may pass through input valve 21A. The air then reach the insides of the body of the bag 28. The bag 28 is compressed by the paddle 32, which causes the air to flow through the output valve 21B of the bag 28 towards the mask 26.

In some embodiments, the paddle 32 has a convex shape. Specifically, as discussed previously, the paddle 32 may have a convex contact surface 50. Additionally, the paddle 32 may be oriented relative to the bag 28 such that their longitudinal axes 29 and 52 are substantially aligned. Thus, as the actuator (e.g., the motor 40) causes the strap 43 to tighten, the paddle 32 compresses the bag 28 and the bag 28 deforms in a predictable manner. The inventors discovered that the arrangement of the convex paddle 52 aligned with the longitudinal axis of the bas 28 minimizes dead space and allows for precision control of the volume expelled. Furthermore, in illustrative embodiments, the strap 34 provides a mechanically robust system 100 that provides precision control of the speed and volume of compression.

As the air flows out of the bag 28, it flows through the pressure sensor 44, the flow rate sensor 42, and/or the oxygen sensor 46. The pressure sensor 44, the flow rate sensor 42, and/or the oxygen sensor 46 send a signal to the controller 42. The controller 42 controls, among other things, the movement of the actuator based on the input values set in the beginning (e.g., by the user 20 or by automatically by the device 12). The input values include, for example, tidal volume, pressure, volume limit, peak pressure, I:E ratio, inspiratory time, and breathing rate. These values are evaluated by the encoder and the controller 54 to move the actuator.

The signals are fed back to the controller 54, as is described further below. The controller 54 may evaluate the signals and adjust the movement of the actuator, and thus, the amount of air output by the bag 28. The quantified air is passed through the sensors 42, 44, and/or 46 optionally to a second filter, and then to a breathing tube circuit 22, which is connected to the patient 13. The controller 54 also provides values for flow rate, peak pressure, minute volume and oxygen saturation over time, which can be displayed in a graphical or numeric form on the display, the user interface of the device 12, and/or on the mobile app.

In some embodiments, the sensors 42-46 may send a message to the controller 54, the display, and/or the alarm. The message may be triggered by a sensor measurement that is not in accordance with the prescribed value for the respiratory parameter (e.g., pressure or volume). The controller 54 may then adjust compression of the bag 28 by the paddle 32 to put the respiratory parameter in accordance with the prescribed value.

Figure 5:
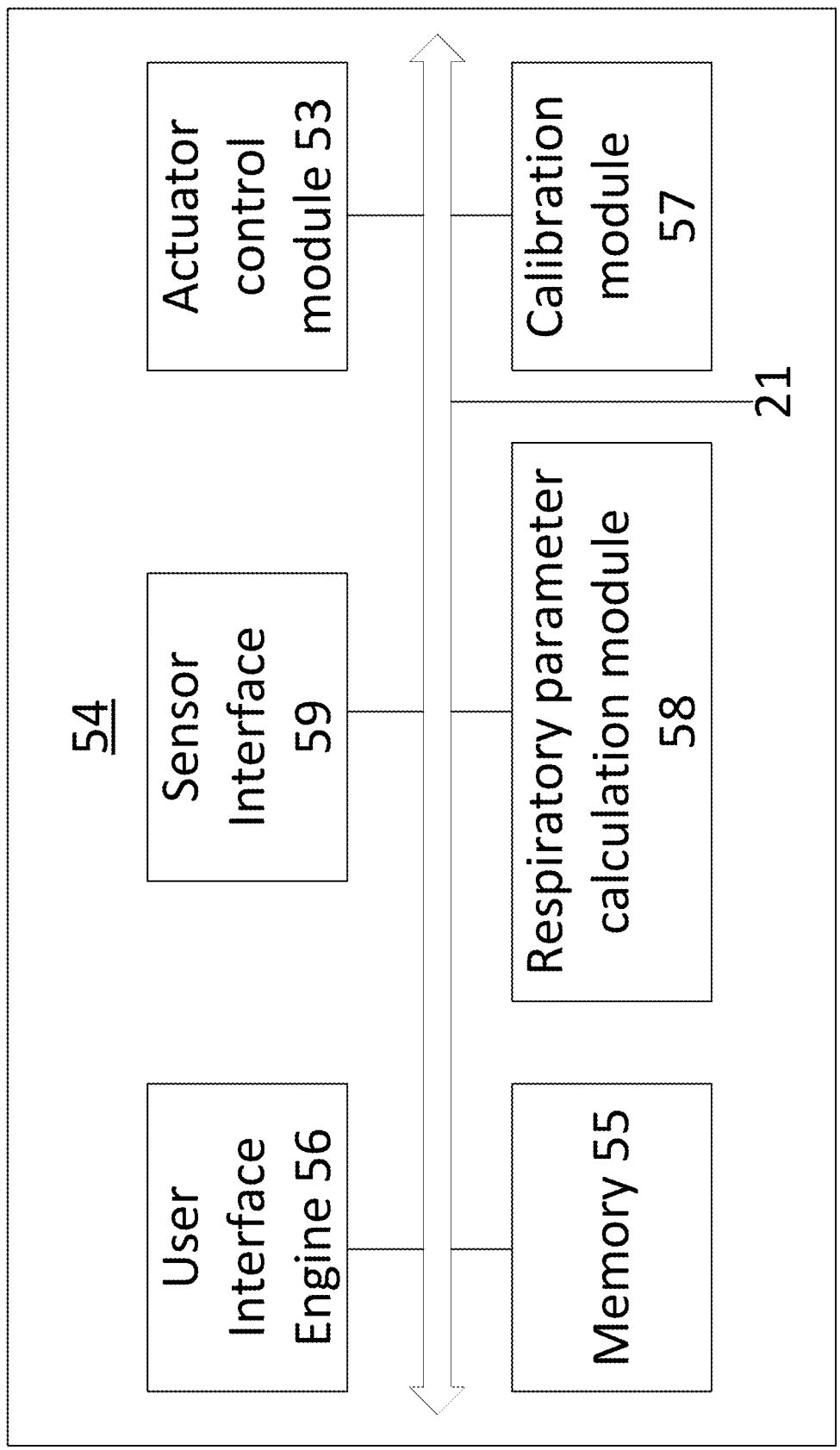
FIG. 5 schematically shows details of the controller that receives feedback from the one or more sensors and that controls the output of the motor in accordance with illustrative embodiments of the invention.

FIG. 5 schematically shows details of the controller 54 that receives feedback from the one or more sensors 42 and 44, and that controls the output of the motor 40 in accordance with illustrative embodiments of the invention. The controller 54 is configured to, among other things, control the output of the motor 40. To that end, the controller has an actuator control module 53. The actuator control module 53 controls the torque, velocity, position, and/or speed output of the motor 40. Thus, the actuator control module 53 indirectly controls the pressure and flow rate output by the bag 28 (the motor 40 controls position and speed of the paddle 32).

The controller also has a memory 55. The memory 55 may store information relating to the input parameters, the data received from the sensor interface, and/or formulas used to calculate respiratory parameters.

The controller 54 controls the motor 40 in accordance with prescribed values for various respiratory parameters. To that end, the controller 54 has a user interface engine 56, which may receive inputs, for example, from the physical user interface 23. Additionally, the user interface engine 56 may communicate with the user interface 23 and/or the display 19. For example, the user interface engine 56 may receive a message from the signal interface 59 indicating that one or more of the sensors 42, 44, and/or 46 is detecting an out of parameter condition. For example, the oxygen sensor 46 may detect that the oxygen is too low. As an additional example, the pressure sensor 44 may detect that the pressure is too high. The user interface engine 56 may send an alarm to the physical user interface 23, the electronic mobile device 19, or another display, informing the user 20 that the out of condition state exists. Additionally, in some embodiments, the out of parameter condition may be sent to the actuator control module 53. The actuator control module 53 may adjust the operation of the actuator (e.g., by stopping the compression of the bag 28 completely).

The user interface engine 56 receives the user 20 selection of one or more respiratory parameters, including Output Volume, Pressure Limit, Breathing rate, Inhalation to exhalation ratio, and/or inspiratory time. The user 20 may enter specific values for each of the respiratory parameters, and the motor 40 is correspondingly controlled to output air from the bag 28 in accordance with those parameters.

Alternatively, the user 20 may enter information about the patient 13 (e.g., height, weight, sex), and a parameter calculation module 58 may calculate appropriate respiratory parameters for the patient 13. To that end, the calculation module 58 may communicate with the memory to access formulas known in the literature.

The controller 54 also has a calibration module 57. As will be described further below, with reference to FIG. 6, the device 12 may use a calibration process. The calibration module receives respiratory parameters and/or a ventilation mode from the user interface engine 56. The calibration module 57 instructs the actuator control module 53 to begin ventilation. A sensor interface 59 interfaces with the various sensors 42, 44, and/or 46, and receives data about the output air (e.g., pressure, flow rate, oxygen level, etc.). The calibration module 57 determines if the output air is in compliance with prescribed values for the respiratory parameters. If not, the calibration module 57 sends a signal to the actuator control module 53 to adjust the signal sent to the motor 40.

Each of the above-described components is operatively connected by any conventional interconnect mechanism.

FIG. 5 simply shows a bus 51 communicating each of the components. Those skilled in the art should understand that this generalized representation can be modified to include other conventional direct or indirect connections. Accordingly, discussion of a bus is not intended to limit various embodiments.

Indeed, it should be noted that FIG. 5 only schematically shows each of these components. Those skilled in the art should understand that each of these components can be implemented in a variety of conventional manners, such as by using hardware, software, or a combination of hardware and software, across one or more other functional components. For example, the actuator control module 53 may be implemented using a plurality of microprocessors executing firmware. As another example, the calibration module 57 may be implemented using one or more application specific integrated circuits (i.e., "ASICs") and related software, or a combination of ASICs, discrete electronic components (e.g., transistors), and microprocessors. Accordingly, the representation of the components in a single box of FIG. 5 is for simplicity purposes only. In fact, in some embodiments, the actuator control module 53 is distributed across a plurality of different machines—not necessarily within the same housing or chassis. Additionally, in some embodiments, components shown as separate (such as the calculation module 58 and the calibration module 57) may be replaced by a single component. Furthermore, certain components and sub-components in FIG. 5 are optional. For example, some embodiments may not use the parameter calculation module 58.

It should be reiterated that the representation of FIG. 5 is a significantly simplified representation of the ventilation controller 54. Those skilled in the art should understand that such a device may have other physical and functional components, such as central processing units, other packet processing modules, and short-term memory. Accordingly, this discussion is not intended to suggest that FIG. 5 represents all of the elements of the ventilation controller 54.

Figure 6:
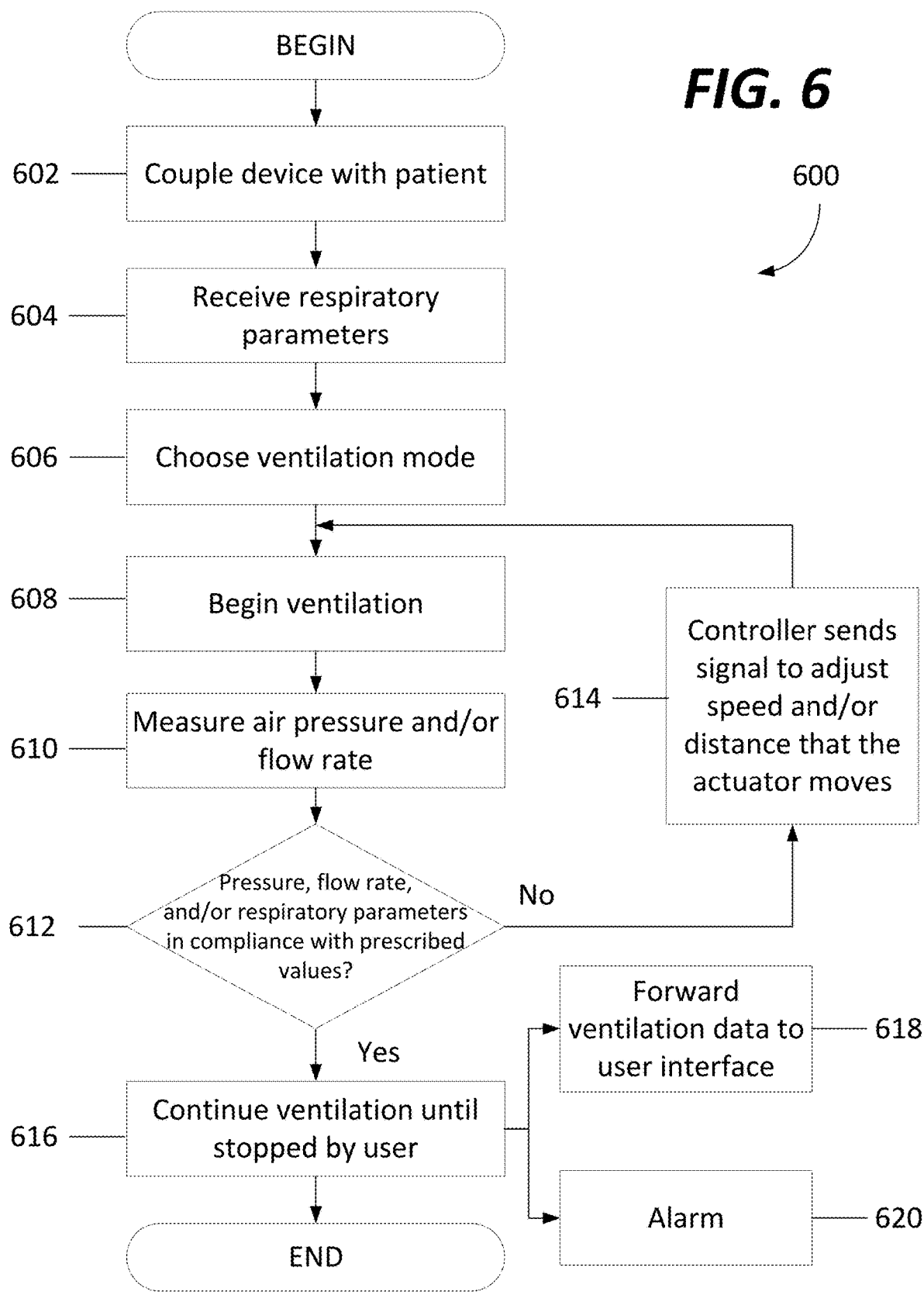
FIG. 6 shows one embodiment of a process of ventilating the patient in accordance with prescribed values for respiratory parameters.

FIG. 6 shows one embodiment of a process 600 of ventilating the patient 13 in accordance with prescribed values for respiratory parameters. It should be noted that this process is substantially simplified from a longer process that normally would be. As such, the process may have additional steps that are not discussed. In addition, some steps may be optional, performed in a different order, or in parallel with each other. For example, step 602 may come after step 608. As another example, step 620 may start after step 608. Furthermore, some of these steps may be optional in some embodiments. Accordingly, discussion of this process is illustrative and not intended to limit various embodiments of the invention. Accordingly, the process 600 is merely exemplary of one process in accordance with illustrative embodiments of the invention. Those skilled in the art therefore can modify the process as appropriate.

The process 600 begins at step 602, which couples the output of the device 12 with the patient's 13 respiratory tract. Specifically, the output valve 21B shown in FIG. 1 is securely connected via the tubing 22 and the mask 26 over the patient's 13 mouth and nose. The process then proceeds to step 604, which receives the respiratory parameters. As mentioned previously, the user may manually enter values for the respiratory parameters through the user interface 23, and/or the parameter calculation module 58 may generate values for the parameters after providing information about the patient 13. In order to receive the respiratory parameters, the device 12 may be powered on using the on and off switch (not shown). The user interface 23 may comprise an LCD screen that displays instructions. Additionally, or alternatively, the user interface 23 may be on a user's mobile device (e.g., smartphone). In some embodiments, step 602 may come after the device 12 is calibrated.

The user 20 inputs the respiratory parameters (e.g., the user 20 may rotate the knob(s) to adjust the inputs) based on the patient's 13 clinical state. The respiratory parameters may include, for example, tidal volume, peak pressure, breathing rate, and/or I:E ratio. In illustrative embodiments, the user 20 may input one or more respiratory parameters including: tidal volume, pressure, volume limit, peak pressure, I:E ratio, inspiratory time, and/or breathing rate of the oxygen and/or the air flowing through the output valve 21B to the patient 13. For example, the user 20 may input tidal volume. Alternatively, the user 20 may input the tidal volume and the pressure. Furthermore, the user 20 may input all of the above described respiratory parameters. Specifically, in some embodiments the user 20 may set the tidal volume from between about 0 and about 700 mL, peak pressure from between about 0 and about 50 mm H2O, breathing rate from about 0 to about 35 breaths/min. The user 20 may then confirm the settings by pressing a confirmation button.

The process 600 then proceeds to step 606, where the user 20 selects the ventilation mode. The user 20 may select between volume controlled ventilation, which compresses the bag 28 to deliver air at a selected volume, and/or pressure controlled ventilation, which compresses the bag 28 to deliver air at a selected pressure. Within volume controlled ventilation, there is an additional option to set control ventilation, where the device 12 delivers constant parameters if the patient 13 is not breathing on their own. Alternatively, under volume controlled ventilation, the user 20 may select assist-control ventilation, where the device 12 synchronizes its compressions with the patient's 13 own breathing rhythm In pressure control ventilation mode, the user 20 provides a prescribed value for pressure of the airflow output by the bag 28. The pressure sensor # measures the output pressure to confirm that it is in accordance with the prescribed value. In some embodiments, the prescribed value may be a range or a target value having a built in +/−tolerance. Furthermore, pressure control ventilation may ask the user 20 to select a peak tidal volume and/or peak volume limit.

Volume controlled ventilation delivers a precise amount of volume per inspiration. For example, volume controlled ventilation mode adjusts the output tidal volume (e.g., 400 mL), and allows the user 20 to set limits for peak pressure, breathing rate (e.g., how many breaths in a minute), inspiratory time (e.g., how long to deliver the 0-400 mL breathing), and/or I:E ratio.

The system may also be configured to operate in a pressure controlled ventilation mode. Pressure controlled ventilation mode adjusts the pressure, tidal volume limit, breathing rate, and inspiratory time.

In control ventilation mode, the device 12 is configured to compress the bag 28 on a repeating time cycle. The controller 54 receives the input respiratory parameter values. In some embodiments, the controller 54 assigns a specific distance for the actuator to move based on a calibrated zero value (e.g., using the actuator control module 53). Additionally, the controller 54 may pre-select the time between cycles where the actuator sits at the zero (e.g., bag 28 uncompressed) position. Furthermore, the controller 54 may monitor the speed of the actuator for inhale and exhale cycle over time (e.g., using the calibration module 57). In addition, the controller 53 may take receive real-time data from the sensors through the sensor interface 59. The real-time sensor data may be sent to the actuator control module 53 and used to adjust the compression parameters (e.g., speed) to produce the prescribed flow rate and pressure rate (e.g., by communicating the calibration module 57 with the sensor interface 59 and/or memory 54).

In a similar manner to control ventilation, in assist control ventilation mode the device 12 may also be configured to compress the bag 28 on a repeating time cycle. Accordingly, the patient 13 may be ventilated at a particular breathing rate. However, assist control ventilation may also be trigged by the patient's 13 attempt to inhale on their own. This may find clinical applications, for example, when the patient 13 is not totally sedated. In such a circumstance, the patient may have consciousness and may breathe on their own accord. Illustrative embodiments may provide additional respiratory support that matches the patient's 13 breathing rate. This provides enhanced comfort to the patient 13. Additionally, if the patient 13 cannot breath, or stops drawing breath, on their own, the device 12 may ventilate the patient 13 at the prescribed breathing rate (e.g., selected by the user 20). Thus, in illustrative embodiments, assist control ventilation mode may send the patient 13 a new breath unless the patient 13 overrides it.

In some embodiments, assist control ventilation is triggered when the
patient attempts to inhale while the actuator is at the zero position (e.g., bag 28 is uncompressed) and there is time left before the cycle begins. In assist control ventilation, the sensor continuously monitors for a backflow reading from outlet side (i.e., from the patient 13). If the patient 13 attempts to inhale the values for flow and pressure go beyond the noise threshold and the reading is recorded by the controller 56. The controller 56 may then reset the actuation cycle and appropriately change the time delay between each cycle depending on the patient's 13 inhalation time. The controller 56 then rests the actuation cycle and appropriately changes the time delay between each cycle depending on the patient's 13 inhalation time.

In both assist control ventilation mode and control ventilation mode, the user 20 provides a prescribed value for volume of the air output by the bag 28. The flow rate sensor 42 measures the output air to confirm that it is in accordance with the prescribed value. In some embodiments, the prescribed value may be a range or a target value having a built in +/−tolerance. Furthermore, assist control ventilation mode and control ventilation mode may ask the user 20 to select a peak pressure.

Steps 608-614 calibrate the device 12 when it is initially operated and/or when the values for one or more respiratory parameters are changed. Additionally, this calibration process may occur passively during the operation of the device 12, even after it has been calibrated, to ensure that the device 12 is operating in accordance with the intended respiratory parameters.

At step 608 ventilation begins. Illustrative embodiments compress the bag 28 so that it deforms and collapses in on itself. The inventors discovered that driving a convexly shaped paddle 32 optimized the evacuation of the air volume inside the bag 28. Specifically, illustrative embodiments orient the longitudinal axis 52 of the paddle 28 substantially in parallel to the longitudinal axis 29 of the bag 28. The strap 34 is also partly wrapped around the body of the bag 28. Accordingly, illustrative embodiments aid in consistent and precise delivery of the desired volume at a set pressure while minimizing dead space.

The controller 54 sends a signal to the motor 40 that winds the strap 34 around the spindle 36 at a predetermined velocity. The power delivered to the spindle 36 is governed by the flow rate measured during this step, i.e., if low flow rate is detected, the motor 40 is given more power. Conversely, if high flow is detected the power is reduced (e.g., tapered off gradually). Once the target output volume is achieved, the velocity profile and target positions (amount of rotation required by the motor 40) are recorded as the base compression profile for the start of ventilation. These may be stored in the memory 55 of the controller 54.

After the settings are chosen, the device 12 completes at least one cycle to calibrate based on inputs. For calibration, the actuator exerts force on the bag 28 until a slight flow of air and/or oxygen is detected by the flow rate sensor 42 and/or pressure sensor 44.

At step 610, the air pressure and/or flow rate data from the air coming out of the bag 28 is received by the controller 54. As described previously, the device 12 may have pressure sensor 44 and/or flow rate sensor 42. These sensors 42 and 44 measure the pressure and flow rate, respectively, and provide that data to the controller 54. The device 12 uses dynamic pressure and flow sensor data that is collected in real time to adjust the compression of the bag 28. This data is forwarded to the controller 54. Illustrative embodiments may review data from the last few compression cycles to determine whether the device 12 reaches a steady state governed by the prescribed respiratory parameters (e.g., input by the user or calculated by the calculation module 58).

The process then moves to step 612, which asks whether the pressure, the flow rate, and/or the respiratory parameters are in compliance with the prescribed values. If the input parameters (e.g., tidal volume, peak pressure, breathing rate, etc.) or external variables (e.g., resistance/compliance of the patient's lungs) are causing any of the variables to be out of compliance with the prescribed values, the process 600 moves to step 614.

At step 614, the process 600 compensates for the variance in the pressure, the flow rate, and/or the respiratory parameters by adjusting the speed and/or distance that the actuator moves. For example, the controller 54 may send a signal to the motor 40 requiring that the actuator stroke should be increased.

As an example of volume control adjustment, the device 12 may be set to achieve a tidal volume of 400 mL with every inspiration of the patient 13. After calibration, the device 12 may output the tidal volume of 400 mL. If the patient 13 changes their position on the hospital bed (e.g., as the anesthesia begins to wear off), there may be an increased resistance in the lungs. Accordingly, the actual volume of air that reaches the patient's 13 lungs drops below the desired parameter due to the increased resistance. The feedback mechanism of illustrative embodiments of the invention uses sensors to detect the decrease, and instructs the actuator to move faster and/or more forcefully in real-time to meet the tidal volume goal. This dynamic adjustment of the actuator may continue during the current and future breathing cycles.

As an example of pressure control adjustment, the device 12 may be set to reach a desired pressure of 25 mm H2O. In order to achieve this value, the actuator dynamically course-corrects its velocity throughout the duration of the compression to deliver 22 mm H2O.

After calibration is complete, the user interface 23 (e.g., LCD) may instruct the user 20 to put the mask on or connect the endotracheal tube to the patient 13, if it is not already on the patient 13. The device 12 then begins to deliver the desired amount of air and/or oxygen to the patient 13 in accordance with the prescribed respiratory parameters. If the settings need to be changed, the user 20 may pause the device 12 and re-adjust the input settings. The user 20 may then re-start the device 12, which delivers the new levels of desired air and/or oxygen.

If the pressure, the flow rate, and/or the respiratory parameters are in compliance with the prescribed parameters, the process moves to step 616, where ventilation is continued until the user 20 stops the device 12.

Optionally, the process may move to step 618, where the device 12 sends a signal (e.g., to a mobile device application) where the flow rate and pressure data are recorded and displayed over time. This provides users 20 with information relating to the ventilation delivery pattern of the patient 13. To turn the device 12 off, the user takes the mask/endotracheal tube off the patient and turns off the power switch.

Additionally, the process may optionally move to step 620. In case the values of the desired air and/or oxygen delivered deviates, step 620 causes alarms to be triggered to notify the user 20. These alarms will trigger if the readings are, for example, above and/or below tidal volume input and peak pressure. Although shown near the end of process 600, steps 618-620 may be ongoing from the beginning of the process.

A person of skill in the art should understand that illustrative embodiments provide a number of advantages. For example, illustrative embodiments provide superior control over the ventilation delivered to the patient by the bag 28. Specifically, feedback sensors 42 and 44 for pressure and flow rate are detected and used to adjust the tidal volume, peak pressure, breathing rate and/or I:E ratio to match the selected inputs. Illustrative embodiments also increase patient safety by using alarm sensors to detect whether an accurate amount of air and/or oxygen is delivered to the patient.

Illustrative embodiments provide a further advantage in that they integrate with equipment already in common use in the hospital. In some embodiments, the output valves are able to integrate with both ends of the breathing circuit and mask, which allows the device to be easily used in a hospital setting. Furthermore, illustrative embodiments are portable. To that end, the device may be formed from light materials, including plastics, and the components may be compactly arranged.

Other advantages of illustrative embodiments include simple functionality. For example, the input controls may include three knobs, one confirmation button, and one slider switch to change between ventilation modes and a power button. Furthermore, a LCD may be placed on the device 12 to display real time readings. Illustrative embodiments are also user friendly. For example, two back doors allow for easy access to internal components, including the bag 28 and the batteries. Furthermore, many of the components of the device are available in low resource settings, such as the bag 28, batteries, and other internal components.

Yet another advantage of illustrative embodiments is remote monitoring of ventilation data. This is achieved, for example, via a mobile application. Illustrative embodiments have a graphical display of data, such as tidal volume, I:E ratio, peak pressure, breathing rate, % oxygen saturation and minute volume ventilation. This provides real time monitoring of the patient's 13 condition to the doctor and is especially useful in hospitals that are understaffed.

Various embodiments of the invention may be implemented at least in part in any conventional computer programming language. For example, some embodiments may be implemented in a procedural programming language (e.g., "C", "Python", etc.), or in an object oriented programming language (e.g., "C++"). Other embodiments of the invention may be implemented as preprogrammed hardware elements (e.g., application specific integrated circuits, FPGAs, and digital signal processors), or other related components.

In an alternative embodiment, the disclosed apparatus and methods (e.g., see the various flow charts described above) may be implemented as a computer program product for use with a computer system. Such implementation may include a series of computer instructions fixed either on a tangible, non-transitory medium, such as a computer readable medium (e.g., a diskette, CD-ROM, ROM, or fixed disk). The series of computer instructions can embody all or part of the functionality previously described herein with respect to the system.

Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

Among other ways, such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). In fact, some embodiments may be implemented in a software-as-a-service model ("SAAS") or cloud computing model. Of course, some embodiments of the invention may be implemented as a combination of both software (e.g., a computer program product) and hardware. Still other embodiments of the invention are implemented as entirely hardware, or entirely software.

Disclosed embodiments, or portions thereof, may be combined in ways not listed above and/or not explicitly claimed. In addition, embodiments disclosed herein may be suitably practiced, absent any element that is not specifically disclosed herein. Accordingly, the invention should not be viewed as being limited to the disclosed embodiments.

The embodiments of the invention described above are intended to be merely exemplary; numerous variations and modifications will be apparent to those skilled in the art. Such variations and modifications are intended to be within the scope of the present invention as defined by any of the appended claims.

What is claimed is:

1. A system for ventilating a patient comprising:
a flexible bag having a flexible central portion, a first rigid end, and a second rigid end, the flexible bag configured to be inflated through an input valve at the first rigid end that allows oxygen and/or air to flow into the bag, the bag further configured to be deflated through an output valve at the second rigid end that allows the oxygen and/or the air to flow out of the bag;
an actuator including a convex contact surface configured to compress the bag to cause the oxygen and/or the air to flow out of the output valve in accordance with prescribed values for one or more respiratory parameters, the one or more respiratory parameters including tidal volume, pressure, volume limit, peak pressure, I:E ratio, inspiratory time, and/or breathing rate of the oxygen and/or the air flowing through the output valve to a patient, wherein the actuator includes a flexible portion coupled with the convex contact surface, the flexible portion also compressing the bag;
- a controller configured to control the position of the actuator and/or the speed at which the actuator moves in accordance with the prescribed values for the one or more respiratory parameters;
- a pressure sensor coupled to the output valve and configured to determine the pressure of the oxygen and/or the air flowing through the output valve, the pressure sensor further configured to send a pressure signal to the controller;
- a flow rate sensor coupled to the output valve and configured to determine the flow rate of the oxygen and/or the air flowing through the output valve, the flow rate sensor further configured to send a flow rate signal to the controller;
- the controller configured to receive the pressure signal and/or the flow rate signal, and to determine whether the output tidal volume, pressure, volume limit, peak pressure, I:E ratio, inspiratory time, and/or breathing rate are in accordance with the prescribed values, the controller further configured to adjust the position of the actuator and/or the speed at which the actuator moves so as to adjust the output tidal volume, peak pressure, and/or breathing rate to be in accordance with the prescribed values for the one or more respiratory parameters.

2. The system as defined by claim 1, wherein the bag has a longitudinal axis, and the convex contact surface is configured to extend along the longitudinal axis.

3. The system as defined by claim 1, wherein the actuator comprises a spindle that is configured to tighten a strap, the strap being coupled to a paddle having the convex contact surface.

4. The system as defined by claim 3, wherein a first end of the strap is fixed, and a second end of the strap is movable, the paddle being positioned between the first end and the second end.

5. The system as defined by claim 3, wherein the bag is compressed between the paddle and a flat surface.

6. The system as defined by claim 5, wherein the flat surface is a fixed surface.

7. The system as defined by claim 1, further comprising an oxygen sensor coupled to the output valve and configured to determine the oxygen concentration flowing through the output valve, the oxygen sensor further configured to send an oxygen signal to the controller, the controller (1) determining from the oxygen signal whether the patient needs more oxygen, and (2) providing a message to a user interface to titrate oxygen if the user needs more oxygen.

8. The system as defined by claim 1, wherein the controller is configured to receive a selection of a pressure control mode or a volume control mode,
- the pressure control mode including a prescribed value for the pressure, and a prescribed volume limit,
- the volume control mode including a prescribed value for the tidal volume, and a prescribed limit for the peak pressure.

9. The system as defined by claim 8, wherein (a) an alert is triggered and/or (b) the actuator ceases ventilation, when the prescribed limit is exceeded.

10. A method of ventilating a patient comprising:
- controlling an actuator having a convex contact surface, and a flexible portion coupled with the convex contact surface, in accordance with a prescribed value for a respiratory parameter, to compress an inflatable bag having a flexible central portion and two rigid ends, to cause oxygen and/or air to flow out of an output valve of the bag, the respiratory parameter being tidal volume, pressure, volume limit, peak pressure, I:E ratio, inspiratory time, and/or breathing rate of the oxygen and/or the air flowing through the output valve;
- sensing the pressure flowing through the output valve, and sending a pressure signal to the controller;
- sensing flow rate through the output valve, and sending a flow rate signal to the controller;
- adjusting the compression of the actuator as a function of the flow rate signal and/or the pressure signal to adjust the tidal volume, pressure, volume limit, peak pressure, I:E ratio, inspiratory time, and/or breathing rate to be in accordance with the prescribed value.

11. The method of claim 10, wherein the actuator is coupled to a paddle having the convex contact surface.

12. The method of claim 10, wherein the actuator is coupled to a paddle having a longitudinal axis, the method further comprising substantially aligning the longitudinal axis of the paddle with a longitudinal axis of the bag.

13. The method of claim 10, wherein adjusting the compression of the actuator is one of adjusting the position of the actuator and/or the speed at which the actuator moves.

14. The method of claim 10, wherein the actuator comprises a spindle, the spindle being configured to tighten a strap that is coupled to the paddle.

15. A non-transitory computer-readable medium encoded with instructions that, when executed by a processor, establish processes for performing a computer-implemented method of activating an actuator to ventilate a patient, the processes comprising:
- receiving an input of a prescribed value for a respiratory parameter;
- controlling an actuator coupled to a paddle having a convex contact surface to compress an inflatable bag to cause oxygen and/or air to flow out of an output valve of the bag in accordance with the prescribed value for the respiratory parameter, the actuator including a flexible portion coupled with the convex contact surface, the flexible portion also compressing the bag;
- interfacing with (1) a pressure sensor that measures the pressure of the oxygen and/or the air flowing through the output valve, and/or (2) a flow rate sensor coupled to the output valve and configured to determine the flow rate of the oxygen and/or the air flowing through the output valve;
- receiving a pressure signal from the pressure sensor and/or a flow rate signal from the flow rate sensor;
- adjusting the controlling of the actuator to compress the bag to put the output value for the respiratory parameter in accordance with the prescribed value.

16. The non-transitory computer-readable medium of claim 15, wherein the respiratory parameter is tidal volume, pressure, volume limit, peak pressure, I:E ratio, inspiratory time, and/or the air flowing through the output valve.

17. The non-transitory computer-readable medium of claim 15, wherein the actuator is coupled to a paddle having a longitudinal axis, further comprising substantially aligning the longitudinal axis of the paddle with a longitudinal axis of the bag.

18. The non-transitory computer-readable medium of claim 15, wherein the actuator comprises a spindle, the spindle being configured to tighten a strap that is coupled to the paddle.

19. The non-transitory computer-readable medium of claim 15, wherein adjusting the compression of the actuator is one of adjusting the position of the actuator and/or the speed at which the actuator moves.

\* \* \* \* \*